(12) United States Patent
Utsugida et al.

(10) Patent No.: US 11,103,208 B2
(45) Date of Patent: Aug. 31, 2021

(54) PULMONARY FUNCTION MEASUREMENT DEVICE, PULMONARY FUNCTION MEASUREMENT METHOD, AND PULMONARY FUNCTION MEASUREMENT PROGRAM

(71) Applicant: TERUMO KABUSHIKI KAISHA, Tokyo (JP)

(72) Inventors: Tomoki Utsugida, Machida (JP); Shin Maki, Ebina (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 297 days.

(21) Appl. No.: 16/138,546

(22) Filed: Sep. 21, 2018

(65) Prior Publication Data

US 2019/0021692 A1    Jan. 24, 2019

Related U.S. Application Data (63) Continuation of application No. PCT/JP2017/009786, filed on Mar. 10, 2017.

(30) Foreign Application Priority Data

Mar. 23, 2016   (JP) .............................. JP2016-058364

(51) Int. Cl.
*A61B 8/08*     (2006.01)
*A61B 5/08*     (2006.01)
(Continued)

(52) U.S. Cl.
CPC ................. *A61B 8/08* (2013.01); *A61B 5/08* (2013.01); *A61B 5/0803* (2013.01); *A61B 8/461* (2013.01);
(Continued)

(58) Field of Classification Search
CPC ....... A61B 5/0205; A61B 5/08; A61B 5/0803; A61B 8/08; A61B 8/15; A61B 8/461; A61B 8/4477; A61B 8/5223; A61B 7/003
See application file for complete search history.

(56) References Cited

U.S. PATENT DOCUMENTS

2002/0151789 A1  10/2002 Mansy et al.
2009/0036777 A1   2/2009 Zhang et al.
(Continued)

FOREIGN PATENT DOCUMENTS

JP     2002509747 A     4/2002
JP    20100534548 A    11/2010

OTHER PUBLICATIONS

Notice of Reasons for Refusal issued by the Japanese Patent Office in corresponding Japanese Patent Application No. 2018-507223 dated Jun. 29, 2020 (4 pages including partial English translation).

(Continued)

*Primary Examiner* — Daniel L Cerioni
*Assistant Examiner* — Raymond P Dulman
(74) *Attorney, Agent, or Firm* — Buchanan Ingersoll & Rooney PC (57) ABSTRACT

A pulmonary function measurement device, a pulmonary function measurement method, and a pulmonary function measurement program are disclosed. The pulmonary function measurement device for measuring data for evaluating a pulmonary function includes a sound output unit configured to be fixed to a body surface on one of front and rear sides of a lung, and outputs a sound toward the lung; a sound detection unit configured to be fixed to a body surface on one of the front and rear sides of the lung different from the side on which the sound output unit is to be fixed, and detects the sound from the sound output unit; a measurement unit configured to calculate a transmission time from when the sound output unit outputs the sound to when the sound (Continued)

detection unit detects the sound; and a variation calculation configured to calculate the amount of variation in the transmission time.

17 Claims, 5 Drawing Sheets

(51) Int. Cl.
    *A61B 8/00*        (2006.01)
    *A61B 7/00*        (2006.01)
    *A61B 5/0205*    (2006.01)
    *A61B 8/15*        (2006.01)

(52) U.S. Cl.
    CPC .......... *A61B 8/5223* (2013.01); *A61B 5/0205* (2013.01); *A61B 7/003* (2013.01); *A61B 8/15* (2013.01); *A61B 8/4477* (2013.01)

(56) References Cited

U.S. PATENT DOCUMENTS

2013/0016240 A1    1/2013    Sasaki et al.
2013/0018240 A1    1/2013    McCoy
2013/0116561 A1*  5/2013    Rothberg ................. A61B 8/13
                                                            600/438
2015/0209001 A1*  7/2015    Wolf ..................... A61B 8/085
                                                            600/301
2015/0342518 A1* 12/2015   Persidsky ............ A61B 5/6831
                                                            600/534
2016/0051205 A1*  2/2016    Al-Ali .................... A61B 5/742
                                                            600/301

OTHER PUBLICATIONS

An English Translation of the International Search Report (Form PCT/ISA/210) and the Written Opinion of the International Searching Authority (Form PCT/ISA/237) dated Jun. 6, 2017, by the Japanese Patent Office in rresponding International Application No. PCT/JP2017/009786. (6 pages).

International Search Report (PCT/ISA/210) dated Jun. 6, 2017, by the Japanese Patent Office as the International Searching Authority for International Application No. PCT/JP2017/009786.

Written Opinion (PCT/ISA/237) dated Jun. 6, 2017, by the Japanese Patent Office as the International Searching Authority for International Application No. PCT/JP2017/009786.

* cited by examiner

PULMONARY FUNCTION MEASUREMENT DEVICE, PULMONARY FUNCTION MEASUREMENT METHOD, AND PULMONARY FUNCTION MEASUREMENT PROGRAM

CROSS-REFERENCES TO RELATED APPLICATIONS

This application is a continuation of International Application No. PCT/JP2017/009786 filed on Mar. 10, 2017, which claims priority to Japanese Application No. 2016-058364 filed on Mar. 23, 2016, the entire content of both of which is incorporated herein by reference.

FIELD OF THE INVENTION

The present disclosure generally relates to a pulmonary function measurement device, a pulmonary function measurement method, and a pulmonary function measurement program, which are for measuring data for evaluating a pulmonary function.

BACKGROUND DISCUSSION

When the cardiac output decreases due to insufficient action of the heart, a mechanism of the living body for maintaining the cardiac output works to suppress the decrease in the cardiac output. However, burdens are placed on various portions of the body, and as a result, a symptom may appear. Heart failure is not a disease name, but indicates such a "state of the body generated as a result of insufficient action of the heart".

When heart failure occurs, a cardiac pump function is decreased, so that blood cannot be sent out sufficiently. Therefore, the blood that cannot be sent out from the heart is accumulated in an organ immediately before the heart in the circulation system, so that a symptom appears. In the case of a right heart failure, a symptom appears in the general circulation system, and in the case of a left heart failure, a symptom appears in the pulmonary circulation system. In the case of the left heart failure, the blood that flows from the lungs to the left heart is stagnated in the lungs, so that the liquid component of the blood in the lungs oozes (i.e., seeps) out into lung tissue, and the lungs become a congested state.

It is difficult to be aware of symptoms of a heart failure. Accordingly, an occurrence of an acute exacerbation such as a myocardial infarction brings the awareness of the heart failure for the first time. Therefore, there is a demand for a method that can rather easily monitor a heart failure and can help identify heart failure at a rather early stage.

For this purpose, various devices that measure the state of the lungs have been proposed. For example, JP-T-2010-534548 (the term "JP-T" as used herein means a published Japanese translation of a PCT application) describes a device that outputs a sound toward lungs for evaluating a cardiac function, and receives the reflected sound, thereby measuring a state of the lungs.

The device described in JP-T-2010-534548 needs to be embedded in a body, has a relatively high invasiveness, and places an increased burden on a measurement subject.

SUMMARY

A pulmonary function measurement device, a pulmonary function measurement method, and a pulmonary function measurement program are disclosed that are non-invasive and can operate with a relatively reduced burden on a measurement subject.

A pulmonary function measurement device is disclosed for measuring data for evaluating a pulmonary function, the pulmonary function measurement device including: a sound output unit configured to be fixed to a body surface on one of front and rear sides of a lung, and outputs a sound toward the lung; a sound detection unit configured to be fixed to a body surface on one of the front and rear sides of the lung different from the side on which the sound output unit is to be fixed, and detects a sound from the sound output unit; a measurement unit configured to calculate a transmission time from when the sound output unit outputs the sound to when the sound detection unit detects the sound; and a variation calculation unit configured to calculate an amount of variation in the transmission time.

A pulmonary function measurement method is disclosed for measuring data for evaluating a pulmonary function, the pulmonary function measurement method including: outputting, toward a lung, a sound from a body surface on one of front and rear sides of the lung; detecting a sound at a body surface on one of the front and rear sides of the lung different from the side on which the sound is output; calculating a transmission time from when the sound is output to when the sound is detected; and calculating an amount of variation in the transmission time.

A pulmonary function measurement program stored in a non-transitory, tangible computer readable recording medium configured to be executable by a computer to measure data for evaluating a pulmonary function is disclosed, the pulmonary function measurement program including: causing a sound output unit to output a sound toward a lung; receiving a detection result from a sound detection unit that detects a sound; calculating a transmission time from when the sound is output to when the sound is detected; and calculating an amount of variation in the transmission time.

The pulmonary function measurement device, the pulmonary function measurement method, and the pulmonary function measurement program configured as described above observe changes in the shape of the lungs, which serve as an index of the decrease in a pulmonary function, using the transmission time of the sound that passes through the lungs, and thus are relatively non-invasive and can operate with a rather reduced burden on the measurement subject.

BRIEF DESCRIPTION OF THE DRAWINGS

FIGS. 2A and 2B are side views respectively illustrating states where the pulmonary function measurement device is attached to a measurement subject, wherein FIG. 2A illustrates the state of inspiration, and FIG. 2B illustrates the state of expiration.

DETAILED DESCRIPTION

Hereinafter, with reference to the drawings, an embodiment of the disclosure will be described. Note that, the size ratio in the drawings may be exaggerated for convenience of explanation, and may be different from the actual ratio in some cases.

A pulmonary function measurement device 10 according to an embodiment of the disclosure is a device capable of collecting times (transmission times) required for a sound to pass from one of front and rear sides of a lung to the other side on a relatively long term basis and capable of determining the presence or absence of a left heart failure daily, for example. The pulmonary function measurement device 10 can be used by a measurement subject himself/herself on a daily basis, and can monitor a change in cardiac state on a relatively long term basis. Moreover, the pulmonary function measurement device 10 can be also used for a short-term monitoring use in which the presence or absence of a heart failure is determined according to an instruction by a doctor during a period of about two or three days to allow a diagnosis with relatively higher accuracy than that in a short time on arrival at the hospital. In the present description, a "front side" of a body means the side where a face is oriented, and a "rear side" of the body means the side where a back is oriented. Note that, the pulmonary function measurement device 10 according to the present embodiment can measure a pulmonary function with the objective of evaluating a cardiac function, but may measure the degree of lung congestion without the objective of evaluating a cardiac function.

Figure 1:
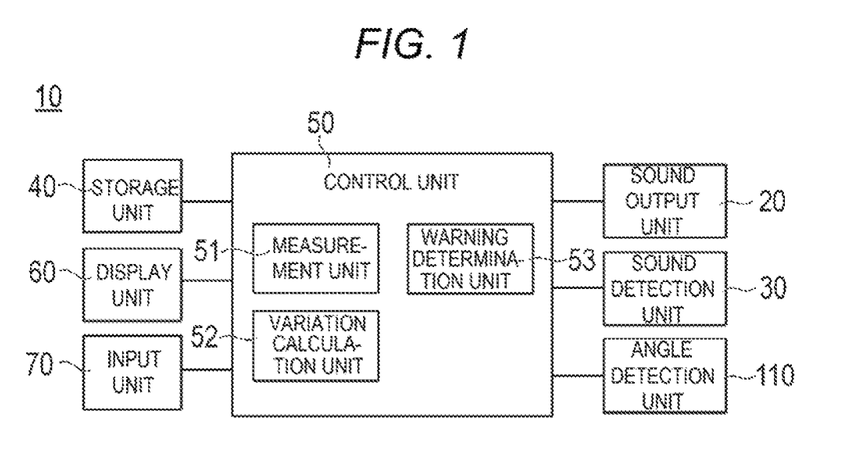
FIG. 1 is a block diagram illustrating a pulmonary function measurement device according to an embodiment.
Figure 2A:
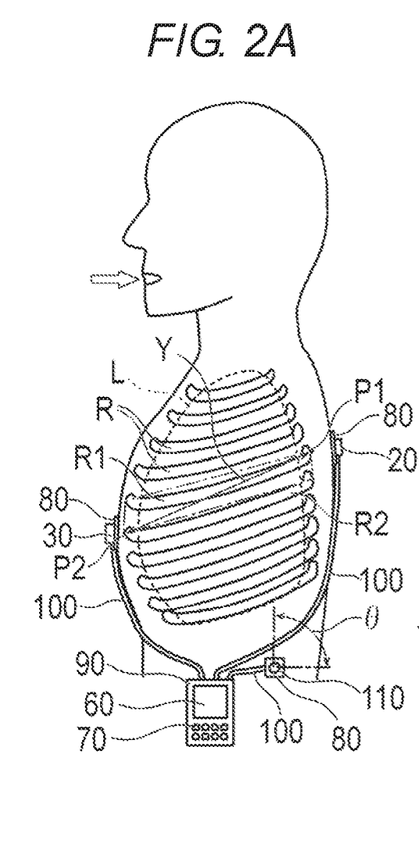
Figure 2B:
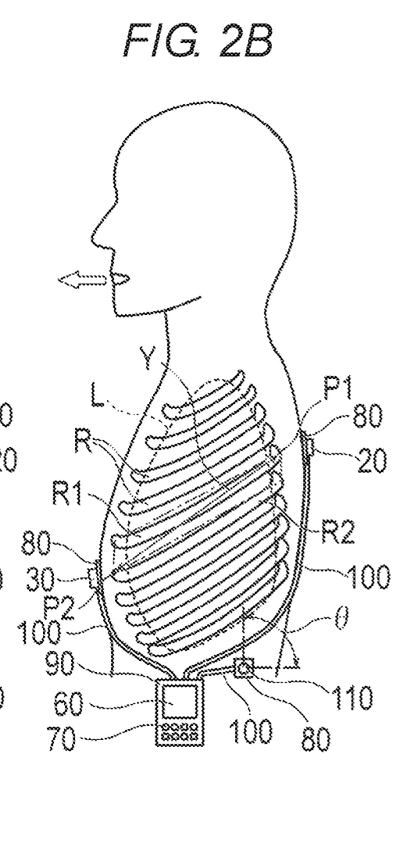
Figure 3:
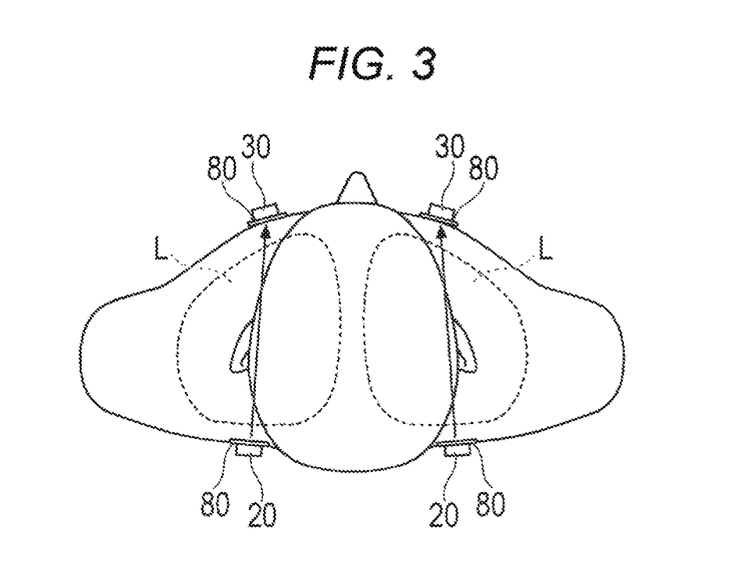
FIG. 3 is a top view illustrating a state where the pulmonary function measurement device is attached to the measurement subject.

The pulmonary function measurement device 10 includes, as illustrated in FIGS. 1 to 3, a sound output unit 20 that outputs a sound, a sound detection unit 30 that detects a sound, a storage unit 40, a control unit 50, an input unit 70, a display unit 60, and an angle detection unit 110. The pulmonary function measurement device 10 is further provided with a fixing member 80 for fixing the sound output unit 20, the sound detection unit 30, and the angle detection unit 110 to a body surface, a housing (or device main body) 90 that contains the storage unit 40, the control unit 50, the input unit 70, and the display unit 60, and a cable 100 that connects the sound output unit 20, the sound detection unit 30, and the angle detection unit 110 to the housing 90. The control unit 50 and the storage unit (i.e., memory) 40 form a computer for executing a program to measure data for evaluating a pulmonary function as disclosed. Accordingly, an operation of the pulmonary function measurement device 10 can be executed by the program on the control unit 50 and the storage unit 40.

The sound output unit 20 is a speaker including an oscillator for outputting a sound and an amplifier. The sound output from the sound output unit 20 is used for measuring the time required for the sound to pass through the lung. The sound output unit 20 is fixed (i.e., attached) to a side in front of or behind the lung (a side behind the lung in the present embodiment) using a fixing member 80. For example, the fixing member 80 can be an adhesive tape. In accordance with an exemplary embodiment, the output unit 20 can include two sound output units 20, and wherein the two output units 20 output a sound for each of the left and right lungs L, respectively. The sound output unit 20 outputs a sound, in response to an instruction from the control unit 50, with an interval (sampling period) set in advance or input from the input unit 70. A plurality of sampling, for example, in one breath can be preferably performed in order to obtain data of a deformation amount of the lung in the breathing. The sampling period is, for example, 0.1 second to 1 second, although not particularly limited. Note that, the sound output unit 20 may successively output sounds of a predetermined waveform without outputting sounds with the sampling period.

The frequency of the sound output from the sound output unit 20 can be, for example, 50 Hz to 500 Hz (Hertz), although not particularly limited as long as the sound can pass through the body. The waveform of the sound output from the sound output unit 20 is preferably a shape that allows accurate identification of the timing when the sound reaches the sound detection unit 30, such as a sine wave or a pulse wave, although not particularly limited as long as the sound detection unit 30 can detect the sound. Moreover, the sounds output from the two sound output units 20 may have different frequencies, waveforms, output timings, and the like so as to easily identify for which of the sound output units 20 outputs the sound, from a detection result of the sound.

The sound detection unit 30 is a microphone for detecting a sound that is output from the sound output unit 20 and passes through the lung L. In accordance with an exemplary embodiment, two sound detection units 30 corresponding to the left and right lungs L are provided. The sound detection unit 30 is fixed (i.e., attached) to an opposite side (front side in the present embodiment), out of the front side and the rear side of the lung L, of a side to which the sound output unit 20 is attached by the fixing member 80. The sound detection unit 30 that is fixed to the front side of the left lung L detects a sound output from the sound output unit 20 that is fixed to the rear side of the left lung L. The sound detection unit 30 that is fixed to the front side of the right lung L detects a sound output from the sound output unit 20 that is fixed to the rear side of the right lung L. The sound detection unit 30 transmits a detection result to a measurement unit 51 in the control unit 50.

The sound output unit 20 and the sound detection unit 30 as a pair are respectively fixed (i.e., attached) to positions in which the left or right lung L is sandwiched between the sound output unit 20 and the sound detection unit 30 and a distance between the sound output unit 20 and the sound detection unit 30 varies by the breathing. The inclination of ribs R that surround the lungs L changes depending on the volume change of the lungs L. Each rib R is typically descended lower on the front side than the rear side. The ribs R are inclined in the inspiration to raise the front side of the ribs R, as illustrated in FIG. 2A. Further, the ribs R are inclined in the expiration to lower the front side of the ribs R, as illustrated in FIG. 2B. Accordingly, any two ribs R1 and R2 on the same side (left side in FIG. 2) out of the left and right sides of the body constitute a substantial parallelogram when observed from the lateral direction of the body. A distance Y between a position P1 on the rear side of the upper rib R1 and a position P2 on the front side of the lower rib R2 varies with the change of the inclinations of the ribs R1 and R2. In other words, the distance Y becomes longer in the inspiration as illustrated in FIG. 2A, and becomes shorter in the expiration as illustrated in FIG. 2B. Accordingly, the sound output unit 20 and the sound detection unit 30 are preferably fixed to the front side and the rear side of end portions of the different ribs R1 and R2, respectively, such that the distance Y is likely to vary by the breathing. Further, the sound output unit 20 and the sound detection unit 30 are preferably fixed to the same positions on the body surface every time. Note that, the positions to which the sound output unit 20 and the sound detection unit 30 are fixed are not particularly limited as long as the distance between the positions varies by the breathing. Accordingly, the positions to which the sound output unit 20 and the sound detection unit 30 are fixed do not need to accurately correspond to the positions of the ribs R1 and R2. For example, the sound output unit 20 and the sound detection unit 30 may be fixed between two adjacent ribs R.

The angle detection unit 110 is a sensor that detects an inclination angle θ of the long axis of the body with respect to the horizontal plane. The angle detection unit 110 transmits a detected signal to the control unit 50 through the cable 100. A position to which the angle detection unit 110 is fixed is not particularly limited as long as the angle detection unit 110 can measure an inclination of the body. The angle detection unit 110 is not particularly limited as long as the angle detection unit 110 can detect the inclination angle θ of the body, and is an acceleration sensor, for example.

The housing (or device main body) 90 is connected to the sound output unit 20, the sound detection unit 30, and the angle detection unit 110 with the cable 100, as illustrated in FIGS. 1, 2A, and 2B. The device main body 90 is attached to a measurement subject with a belt, for example.

The storage unit (i.e., memory) 40 stores various kinds of operation programs such as a measurement program that is executed in the control unit 50, and various kinds of parameters (for example, thresholds). The storage unit 40 further stores data detected by the sound detection unit 30 and the angle detection unit 110, and data calculated by the control unit 50.

The control unit 50 can include the measurement unit 51, a variation calculation unit 52, and a warning determination unit 53. The control unit 50 includes a central processing unit (CPU) and an operation program. The control unit 50 controls in a centralized manner operations of the sound output unit 20, the sound detection unit 30, the angle detection unit 110, the storage unit 40, the measurement unit 51, the variation calculation unit 52, the warning determination unit 53, the input unit 70, and the display unit 60.

The measurement unit 51 transmits a signal to the sound output unit 20 to cause the sound output unit 20 to output a sound. The measurement unit 51 receives detection data from the sound detection unit 30. Upon reception of the detection data from the sound detection unit 30, the measurement unit 51 specifies the sound output by the sound output unit 20, from the detection data. For example, the measurement unit 51 can analyze a frequency of the detection data acquired from the sound detection unit 30, and can calculate an amplitude value having a frequency component the same as that of the sound output from the sound output unit 20. The measurement unit 51 can specify that the sound output from the sound output unit 20 has reached in a case where the calculated amplitude value exceeds a threshold set in advance. Moreover, the measurement unit 51 also can specify that the sound output from the sound output unit 20 has reached by identifying a pulse wave or the like the amplitude of which exceeds a threshold set in advance, without analyzing the frequency. After specifying that the sound output from the sound output unit 20 has been detected, the measurement unit 51 calculates the transmission time T from when the sound output unit 20 outputs the sound to when the sound detection unit 30 detects the sound. The measurement unit 51 calculates each transmission time T from the sound output unit 20 and the sound detection unit 30 that correspond to each of the left and right lungs L.

In addition, the measurement unit 51 receives detection data on the inclination angle θ from the angle detection unit 110 when the sound detection unit 30 detects a sound. The measurement unit 51 causes the storage unit 40 to store the transmission time T, the inclination angle θ, and time t when the measurement is performed.

Figure 4:
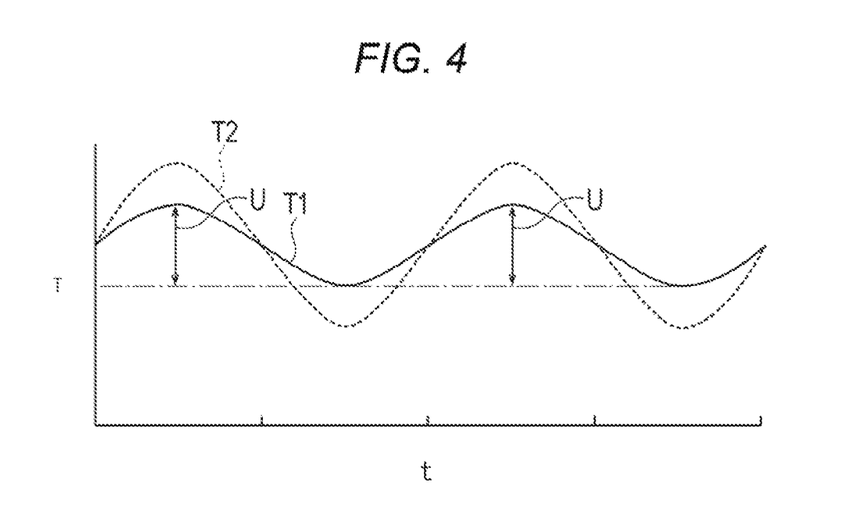
FIG. 4 is a graph illustrating one example of a time change of transmission time measured by the pulmonary function measurement device.

The variation calculation unit 52 calculates a variation amount V of the transmission time T, from data in the transmission time T recorded during a predetermined period of measurement time (for example, 24 hours). The time-series data in the transmission time T has a subtle variation (for example, several hundred Hz) due to an influence by the refraction of the sound in the inner structure of the lungs. Because a variation component by the breathing involves several Hertz (Hz), the variation calculation unit 52 causes the data in the transmission time T to pass through a low-path filter, and acquires only a respiratory component. Note that, the variation calculation unit 52 may subject the data in the transmission time T does not pass through the low-path filter such that data in the transmission time is not subject to a filter processing. The variation calculation unit 52 calculates a unit variation amount U of the transmission time T for every breath as illustrated in FIG. 4, from a time-series waveform of the data in the transmission time T having been subjected to the filter processing. The variation calculation unit 52 calculates a mean value of a plurality of the unit variation amounts U within the measurement time (for example, 24 hours), and sets the mean value as the variation amount V. The variation amount V is an evaluation value corresponding to the magnitude of the deformation of the lung within the measurement time. As a curve T1 in FIG. 4, the smaller variation amount V indicates that the cardiac function is decreased so that the lung is congested, and the deformation of the lung with the breathing is suppressed. Moreover, as a curve T2 in FIG. 4, the larger variation amount V indicates that the cardiac function is normal so that the lung is not congested, and the deformation of the lung with the breathing is relatively smooth. In other words, as the variation amount V is smaller, there is a relatively higher possibility that the cardiac function is abnormal. The variation amount V is calculated for each of the left and right lungs L in the present embodiment.

Note that, the state of the lungs can depend on the inclination angle θ of the body. For example, the gravity acts in different directions between a standing state (θ=90 degrees) and a lying state (θ=0 degrees), so that the shape of the lungs L changes, and the position of an interstitial fluid also changes. Accordingly, there is a possibility that a change in the inclination angle θ of the body may change the transmission time T. Therefore, the variation calculation unit 52 can calculate the unit variation amount U and the variation amount V by reading out the transmission time T and the inclination angle θ from the storage unit 40, and selecting the transmission time T in a case where the inclination angle θ satisfies a predetermined condition, which helps enable the variation calculation unit 52 to calculate the transmission time T that is measured with a posture within a predetermined range, and thus to calculate the unit variation amount U and the variation amount V with relatively high accuracy. The condition for the inclination angle θ is indicated as the following expression (1), for example.

$$45 \text{ degrees} \leq \theta \leq 90 \text{ degrees} \qquad \text{expression (1)}$$

Moreover, the variation calculation unit 52 also can calculate a variation amount of a distance between the sound output unit 20 and the sound detection unit 30 by multiplying the variation amount V of the transmission time T by the sonic velocity.

The warning determination unit 53 compares the variation amount V calculated by the variation calculation unit 52 with a threshold. In accordance with an exemplary embodiment, the threshold is set in advance in the storage unit 40, input from the input unit 70, or calculated from past data, for example. In a case where the variation amount V is lower than the threshold, the warning determination unit 53 determines that the deformation of the lung is relatively small, and the cardiac function (or pulmonary function) is abnormal. In contrast, in a case where the variation amount V is the threshold or more, the warning determination unit 53 determines that the deformation of the lung is relatively large, and the cardiac function (or pulmonary function) is normal. The warning determination unit 53 causes the display unit 60 to display a determination result in the case where the warning determination unit 53 determines that the cardiac function is abnormal. Note that, the threshold in the warning determination unit 53 may be, for example, a lower limit value of an average value of most persons, or may be a value obtained by multiplying a mean value of the measurement subject for the past several months by a coefficient.

The warning determination unit 53 can separately determine two variation amounts V corresponding to the left and right lungs L. Moreover, the warning determination unit 53 may perform the determination using a mean value of the variation amounts V of both of the lungs L. Moreover, the warning determination unit 53 may separately determine the two variation amounts V corresponding to the left and right lungs L, and thereafter may determine that the cardiac function is abnormal in a case where there is an abnormality in either one of the left and right lungs L. Moreover, the warning determination unit 53 may separately determine the two variation amounts V corresponding to the left and right lungs L, and thereafter may determine that the cardiac function is abnormal in a case where there is an abnormality in each of the left and right lungs L.

The input unit 70 is a part where a measurement subject performs an input operation. The input unit 70 includes a switch and buttons, for example. Moreover, the input unit 70 may be, for example, a touch panel, a key board, or a mouse. The input unit 70 is used in inputting and resetting of various kinds of parameters (the threshold, the sampling period, and the determination method), starting and ending of the measurement, selection of a measurement result and a calculation result to be displayed, selection of a graph or a table to be displayed, and other cases.

The display unit 60 is, for example, a display device such as a liquid crystal display (LCD) or an organic electroluminescence (EL) display. The display unit 60 may be, for example, a touch panel that also serves as the input unit 70. The display unit 60 can display on the display unit 60, a value input into the input unit 70, a measurement result, a calculation result, a determination result, or the like as a character, a numerical value, a table, or a graph.

Figure 5:
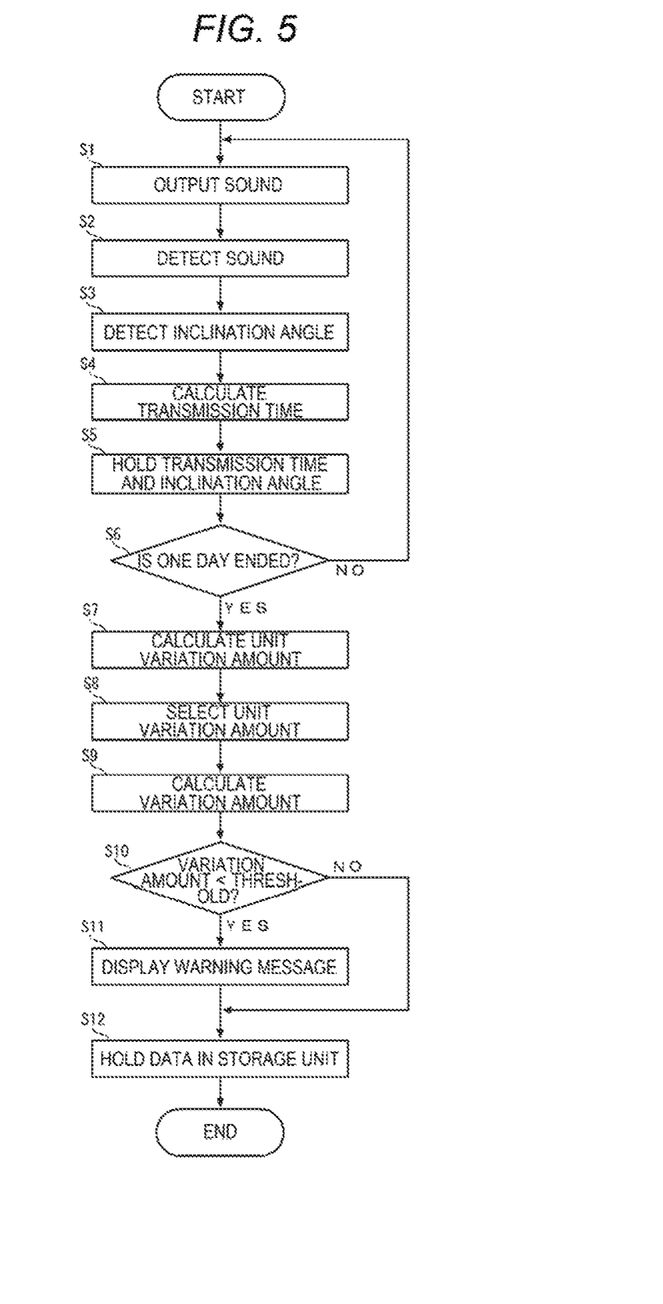
FIG. 5 is a flowchart illustrating a flow of control for the pulmonary function measurement device.

Next, a measurement method using the pulmonary function measurement device 10 according to the present embodiment will be described with reference to a flowchart illustrated in FIG. 5.

A measurement subject firstly fixes (i.e., attaches) the sound output units 20 respectively to the body surfaces on the rear side of the left and right lungs L, as illustrated in FIGS. 2A, 2B, and 3. The measurement subject then fixes (i.e., attaches) the sound detection units 30 respectively to the body surfaces on the front side of the left and right lungs L. The measurement subject fixes the angle detection unit 110 at a place where the long axis of the body can be detected. The positions to which the sound output unit 20 and the sound detection unit 30 are fixed are positions where a distance between the sound output unit 20 and the sound detection unit 30 varies by the breathing. The measurement subject then operates the input unit 70 of the device main body 90, and inputs a parameter such as the measurement time to start the measurement.

The control unit 50 starts the measurement after having received information indicating that the measurement is started from the input unit 70. Accordingly, the measurement unit 51 in the control unit 50 sends a signal to the sound output unit 20, and causes the sound output unit to output a sound for every sampling period (Step 1). The measurement unit 51 then receives a detection result from the sound detection unit 30 (Step 2). The measurement unit 51 then specifies the sound output by the sound output unit 20 from the acquired detection data. The measurement unit 51 then receives a detection result of the inclination angle θ from the angle detection unit 110 (Step 3). The measurement unit 51 subsequently calculates the transmission time T from when the sound output unit 20 outputs the sound to when the sound detection unit 30 detects the sound, in each of the left and right lungs L (Step 4). Thereafter, the measurement unit 51 causes the storage unit 40 to store the transmission time T, the inclination angle θ, and the time t when the measurement is performed (Step 5). The control unit 50 stops, when predetermined measurement time is elapsed, the output of the sound from the sound output unit 20, and stops the detections by the sound detection unit 30 and the angle detection unit 110 (Step 6).

The variation calculation unit 52 then reads the transmission time T, the inclination angle θ, and the time t when the measurement is performed that are stored in the storage unit 40. The variation calculation unit 52 subjects the data in the transmission time T to filter processing. The variation calculation unit 52 then calculates the unit variation amount U of the transmission time T for every breath, from the data in the transmission time T having been subjected to the filter processing (Step 7). The variation calculation unit 52 specifies time t at which the inclination angle θ is within the predetermined range, and selects the unit variation amount U corresponding to the time t (Step 8). Subsequently, the variation calculation unit 52 averages a plurality of the selected unit variation amounts U to calculate the variation amount V (Step 9).

Figure 6:
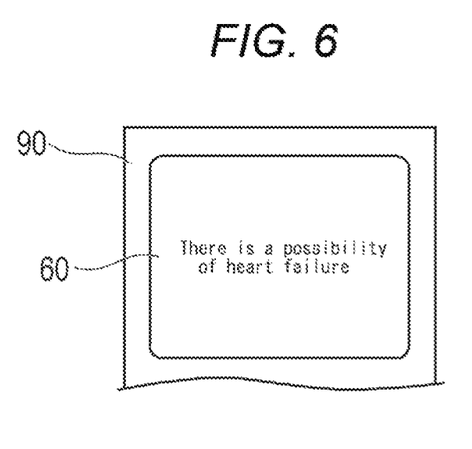
FIG. 6 is a plan view illustrating a display unit on which a warning message is displayed.

The warning determination unit 53 then determines whether the variation amount V of the day calculated by the variation calculation unit 52 is normal (Step 10). In a case where the warning determination unit 53 determines that the variation amount V is abnormal, the warning determination unit 53 causes the display unit 60 to display a warning message as illustrated in FIG. 6 (Step 11). Thereafter, the control unit 50 causes the storage unit 40 to store the calculated unit variation amount U, the calculated variation amount V, the inclination angle θ, and the presence or absence of the abnormality (Step 12). This completes the measurement for one day by the pulmonary function measurement device 10. Note that, the content of the warning message can be set as appropriate.

Figure 7:
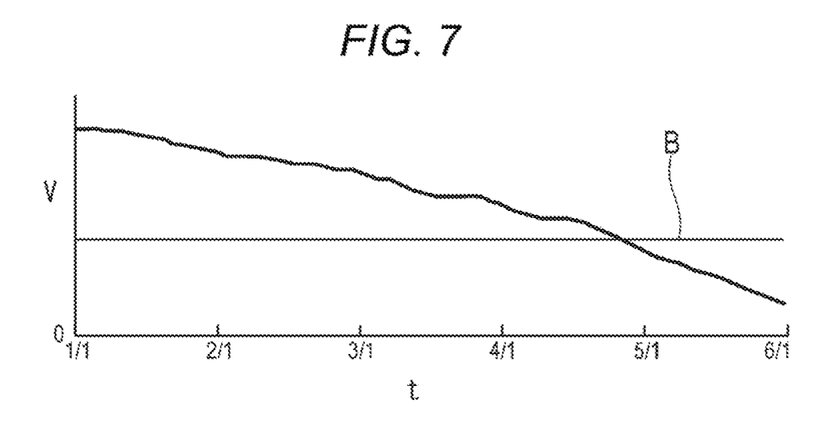
FIG. 7 is a graph illustrating a day-to-day change of a variation amount calculated by the pulmonary function measurement device.

The control unit 50 can cause the display unit 60 to display a time change of the measured variation amount V with past data, as illustrated in FIG. 7. The control unit 50 can display a lower limit B (threshold) for a normal value of the variation amount V as a line on the graph that the display unit 60 is caused to display. In this graph, when the variation amount V becomes lower than the lower limit B, it can be determined that there is a heart failure or there is a possibility of a heart failure. In this manner, the measurement subject himself/herself can easily monitor the degree of the progression of the heart failure over the long term, using the variation amount V as an index indicating the decrease in the cardiac function.

As in the foregoing, the pulmonary function measurement device 10 according to the present embodiment measures data for evaluating a pulmonary function. The pulmonary function measurement device 10 includes: the sound output unit 20 that can be fixed to a body surface on one of front and rear sides of the lung L, and outputs a sound toward the lung L; the sound detection unit 30 that can be fixed to a body surface on one of the front and rear sides of the lung L different from the side on which the sound output unit 20 is to be fixed, and detects the sound from the sound output unit 20; the measurement unit 51 that calculates the transmission time T from when the sound output unit 20 outputs the sound to when the sound detection unit 30 detects the sound; and the variation calculation unit 52 that calculates the amount V of variation in the transmission time T.

The pulmonary function measurement device 10 as described above can calculate the amount V of variation in the transmission time T that is measured using the sound output unit 20 and the sound detection unit 30 being attached to the body surfaces. This allows the magnitude of the shape change of the lungs serving as an index of the decrease in the cardiac function to be observed from the variation amount V, so that easy monitoring of the cardiac function can be achieved. Moreover, the pulmonary function measurement device 10 is non-invasive, and can be configured to be remarkably compact in size, which results in easy portability and operation, so that the pulmonary function measurement device 10 causes relatively less trouble in a daily life even when the long-term monitoring is continued, and places a relatively small burden to a measurement subject.

Moreover, the pulmonary function measurement device 10 further includes the storage unit 40 that can store the variation amount V, so that it is possible to compare the variation amounts V that are measured at different times and calculated, which allows the time change of a cardiac function to be observed, and so that it is possible to achieve rather easy and long-term monitoring of the cardiac function.

Moreover, the sound output unit 20 and the sound detection unit 30 can be fixed (i.e., attached) to positions of a front and a rear of a body that are positions different in a vertical direction and corresponding to the different ribs R, which can change the distance between the sound output unit 20 and the sound detection unit 30 by the breathing, so that it is possible to calculate the variation amount V with relatively high accuracy.

Moreover, the variation calculation unit 52 calculates the unit variation amount U for every breath, and determines the variation amount V as a mean value of a plurality of the unit variation amounts U, which helps remove the fluctuation of measurement for every breath, so that it is possible to obtain the variation amount V suitable for observation.

Moreover, the pulmonary function measurement device 10 further includes the warning determination unit 53 that compares the calculated variation amount V with the lower limit B (threshold), and determines whether to issue a warning, which can help achieve an automatic determination of the presence or absence of a heart failure, and makes it rather easy to monitor the presence or absence of a heart failure.

Moreover, the disclosure includes a pulmonary function measurement method for measuring data for determining the presence or absence of a heart failure. The pulmonary function measurement method includes: a step of outputting, toward a lung L, a sound from a body surface on one of front and rear sides of the lung L; a step of detecting a sound at a body surface on one of the front and rear sides of the lung L different from the side on which the sound output unit 20 is fixed; a step of calculating the transmission time T from when the sound is output to when the sound is detected; and a step of calculating the amount V of variation in the transmission time T.

The pulmonary function measurement method as described above can detect the amount V of variation in the transmission time T of the sound that passes through the lung. Accordingly, it is possible to observe the magnitude of the shape change of the lungs serving as an index of the decrease in the cardiac function with the variation amount V, and thus rather easily monitor the cardiac function. Moreover, the pulmonary function measurement method is non-invasive, and observes a cardiac function with the amount V of variation in the transmission time T of the sound that passes through the lung, so that the pulmonary function measurement method causes less trouble in a daily life even when the long-term monitoring is continued, and places a relatively small burden on a measurement subject.

Moreover, the pulmonary function measurement method further includes: a step of causing the storage unit 40 to store the variation amount V; and a step of reading out, from the storage unit 40, the variation amounts V that are measured at different times and calculated, and comparing the variation amounts V with each other, which allows the time change of a cardiac function to be observed, thereby achieving rather easy and long-term monitoring of the cardiac function.

Moreover, the pulmonary function measurement method further includes a step of fixing, before the step of outputting the sound, the sound output unit 20 and the sound detection unit 30 to positions of a front and a rear of a body that are positions different in a vertical direction and corresponding to the different ribs R, which changes the distance between the sound output unit 20 and the sound detection unit 30 by the breath, and can calculate the variation amount V with relatively high accuracy.

Moreover, the pulmonary function measurement method further includes a step of comparing the calculated variation amount V with the lower limit B (threshold), and determining whether to issue a warning, which helps achieve an automatic determination of the presence or absence of a heart failure, and makes it rather easy to monitor the presence or absence of a heart failure.

Moreover, the disclosure includes a pulmonary function measurement program executable by a computer to measure data for determining the presence or absence of a heart failure. The pulmonary function measurement program includes: a step of causing the sound output unit 20 to output a sound toward the lung L; a step of receiving a detection result from the sound detection unit 30 that detects the sound; a step of calculating the transmission time T from when the sound is output to when the sound is detected; and a step of calculating the amount V of variation in the transmission time T.

The pulmonary function measurement program as described above can detect the amount V of variation in the transmission time T of the sound that passes through the lung. Accordingly, it is possible to observe the magnitude of the shape change of the lungs serving as an index of the decrease in the cardiac function with the variation amount V, and thus rather easily monitor the cardiac function. Moreover, the pulmonary function measurement program is non-invasive, and observes a cardiac function with the amount V of variation in the transmission time T of the sound that passes through the lung, so that the pulmonary function measurement program causes relatively less trouble in a daily life even when the long-term monitoring is continued, and places a relatively small burden to a measurement subject.

Moreover, the pulmonary function measurement program further includes: a step of causing the storage unit 40 to store the variation amount V; and a step reading out, from the storage unit 40, the variation amounts V that are measured at different times and calculated, and comparing the variation amounts V with each other, which allows the time change of a cardiac function to be observed, thereby achieving relatively easy and long-term monitoring of the cardiac function.

Moreover, in the pulmonary function measurement program, the sound output unit 20 and the sound detection unit 30 are fixed to positions of a front and a rear of a body that are positions different in a vertical direction and corresponding to the different ribs R, which changes the distance between the sound output unit 20 and the sound detection unit 30 by the breath, and can calculate the variation amount V with relatively high accuracy.

Moreover, the pulmonary function measurement program further includes a step of comparing the calculated variation amount V with the lower limit B (threshold) set in advance, and determining whether to issue a warning, which achieves an automatic determination of the presence or absence of a heart failure, and makes it rather easy to monitor the presence or absence of a heart failure.

Note that, the disclosure is not limited to the above-described embodiment, but various changes by those skilled in the art can be made within the technical scope of the invention. For example, the housing (or device main body) may be, for example, a mobile terminal such as a smartphone or a tablet terminal and the application (program), or may be a server computer terminal connected to the Internet and the application (program). The sound output unit, the sound detection unit, and the angle detection unit may be wirelessly connected to the device main body using, for example, the communication technology, such as a near field communication (NFC) or Wi-Fi®. Moreover, the sound output unit, the sound detection unit, and the angle detection unit may be integrated with the housing (or device main body). Moreover, the pulmonary function measurement device 10 is a device assumed to be used by a measurement subject himself/herself, however, may be used by a health care worker such as a doctor or a nurse for the measurement subject.

Moreover, although the measurement is performed in both of the left and right lungs L in the abovementioned embodiment, the measurement may be performed in either one of the left and right lungs L. Moreover, a plurality of the sound detection units 30 may be provided in each of the left and right lungs L. A clearance formed between the lungs L and the ribs R may cause such a possibility that the sound cannot be detected. However, the plurality of the sound detection units 30 allows data to be complemented, in a case where one sound detection unit 30 cannot detect a sound, using the detection results by the other sound detection units 30. Moreover, no angle detection unit may be provided. Moreover, although a plurality of the unit variation amounts U for respective breathing are averaged to calculate the variation amount V in the abovementioned embodiment, the unit variation amount U for one breath also can be set as the variation amount V. Moreover, the variation amount V is not a mean value but may be a median value or a mode value (i.e., a number or unit variation amount that appears most often) of a plurality of the unit variation amounts U.

The detailed description above describes a pulmonary function measurement device, a pulmonary function measurement method, and a pulmonary function measurement program, which are for measuring data for evaluating a pulmonary function. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A pulmonary function measurement device for measuring data for evaluating a pulmonary function, the pulmonary function measurement device comprising:
   a sound output unit configured to be fixed to a body surface of a living body on one of front and rear sides of a lung, and to output a sound toward the lung;
   a sound detection unit configured to be fixed to a body surface of the living body on one of the front and rear sides of the lung different from the side on which the sound output unit is configured to be fixed, and to detect the sound from the sound output unit, and wherein the sound output unit and the sound detection unit are configured to be fixed to positions of a front and a rear of the living body that are positions different in a vertical direction and corresponding to different ribs;
   a measurement unit configured to calculate a transmission time from when the sound output unit outputs the sound to when the sound detection unit detects the sound; and
   a variation calculation unit configured to calculate an amount of variation in the transmission time.

2. The pulmonary function measurement device according to claim 1, further comprising:
   a storage unit configured to store the amount of variation in the transmission time; and
   a warning determination unit configured to compare amounts of variation that are measured at different times.

3. The pulmonary function measurement device according to claim 1, wherein the variation calculation unit is configured to calculate a unit amount of variation for every breath, and to determine the amount of variation as a mean value, a median value, or a mode value of a plurality of unit amounts of variation.

4. The pulmonary function measurement device according to claim 1, wherein the sound output unit is configured to output the sound at a frequency of 50 Hz to 500 Hz (Hertz).

5. The pulmonary function measurement device according to claim 1, wherein the sound output unit is configured to output the sound as a sine wave or a pulse wave.

6. The pulmonary function measurement device accordingly to claim 1, wherein the sound output unit includes two sound output units, each of the two sound output units configured to output a sound wave having a frequency, a waveform, and/or an output timing different than the other of the two sound output units.

7. The pulmonary function measurement device according to claim 1, further comprising:
a warning determination unit configured to compare the variation amount calculated by the variation calculation unit with a threshold, the threshold being set in advance in a storage unit, input from an input unit, or calculated from past variation data.

8. The pulmonary function measurement device according to claim 7, further comprising:
a display unit configured to display a determination result when the variation calculation unit determines that the variation amount is smaller than the threshold.

9. The pulmonary function measurement device according to claim 7, wherein the warning determination unit is configured to separately determine two variation amounts corresponding to left and right lungs, respectively.

10. The pulmonary function measurement device according to claim 1, further comprising:
an angle detection unit configured to detect an inclination angle of a long axis of the living body with respect to a horizontal plane.

11. A pulmonary function measurement method for measuring data for evaluating a pulmonary function, the pulmonary function measurement method comprising:
fixing a sound output unit and a sound detection unit to positions of a front and a rear of a living body that are positions different in a vertical direction and corresponding to different ribs;
outputting, toward a lung of the living body, a sound from the sound output unit toward a body surface on one of front and rear sides of the lung;
detecting, with the sound detection unit, a sound at a body surface on one of the front and rear sides of the lung different from the side on which the sound is output;
calculating a transmission time from when the sound is output to when the sound is detected; and
calculating an amount of variation in the transmission time.

12. The pulmonary function measurement method according to claim 11, further comprising:
causing a storage unit to store the amount of variation in the transmission time; and
receiving, from the storage unit, amounts of variation that are calculated at different times, and comparing the amounts of variation with each other with a warning determination unit.

13. The pulmonary function measurement method according to claim 11, further comprising:
detecting an inclination angle of a long axis of the living body with respect to a horizontal plane; and
storing the transmission time, the inclination angle of the living body, and a time when each of the pulmonary function measurements is calculated.

14. The pulmonary function measurement method according to claim 11, further comprising:
comparing the variation amount calculated with a threshold, the threshold being set in advance in a storage unit, input from an input unit, or calculated from past variation data; and
displaying a determination result when the variation amount is smaller than the threshold.

15. The pulmonary function measurement method according to claim 11, further comprising:
determining variation amounts corresponding to left and right lungs, respectively.

16. A pulmonary function measurement program stored in a non-transitory, tangible computer readable recording medium configured to be executable by a computer to measure data for evaluating a pulmonary function, the pulmonary function measurement program comprising:
fixing a sound output unit and a sound detection unit to positions of a front and a rear of a living body that are positions different in a vertical direction and corresponding to different ribs;
causing the sound output unit to output a sound toward a lung of the living body;
receiving a detection result from the sound detection unit that detects a sound;
calculating a transmission time from when the sound is output to when the sound is detected; and
calculating an amount of variation in the transmission time.

17. The pulmonary function measurement program according to claim 16, further comprising:
causing a storage unit to store the amount of variation; and
receiving, from the storage unit, the amounts of variation that are calculated at different times, and comparing the amounts of variation with each other with a warning determination unit.

* * * * *